United States Patent
Nguyen

(10) Patent No.: US 7,303,882 B2
(45) Date of Patent: Dec. 4, 2007

(54) UTILIZATION OF NUCLEOTIDE PROBES IN ELISA PROCEDURE FOR THE QUANTITATIVE DETERMINATION OF BACULOVIRUS TITER

(75) Inventor: Khue Vu Nguyen, San Diego, CA (US)

(73) Assignee: Vista Biologicals Corporation, Carlsbad, CA (US)

( * ) Notice: Subject to any disclaimer, the term of this patent is extended or adjusted under 35 U.S.C. 154(b) by 104 days.

(21) Appl. No.: 11/234,717

(22) Filed: Sep. 26, 2005

(65) Prior Publication Data

US 2007/0072173 A1    Mar. 29, 2007

(51) Int. Cl.
*C12Q 1/68* (2006.01)
(52) U.S. Cl. .......................... 435/6; 435/91.1; 435/91.2
(58) Field of Classification Search ....................... None
See application file for complete search history.

*Primary Examiner*—Gary Benzion
*Assistant Examiner*—Heather G. Calamita

(57) ABSTRACT

To maximize the yield of protein from a baculovirus system, optimal infection of the host cell culture must be achieved; in order to obtain such optimal infection, the titer of the virus inoculation must be known. The present invention is the development of a simple, rapid, and universally applicable titration method that involves the direct detection of the viral DBP gene derived from AcNPV (AcNPV DBP) as a target for quantitative titer determination of baculovirus and the use of biotin specific probes directed to viral DBP gene. The procedure entails the amplification of the AcNPV DBP gene by using the PCR technique in the presence of digoxigenin-11-dUTP from the negative control (non-infected) and infected samples, and the synthesis of the specific biotin label nucleotide probes directed to the AcNPV DBP gene. These specific probes are then used in the Enzyme Linked Immunosorbent Assay (ELISA) using the immobilized streptavidin on polystyrene microtitration plates for the quantitative determination of baculovirus titer. The plot of $O.D._{\lambda=405\ nm}$ against the log of the titer (pfu/mL) generated a straight line. The linear range for titer determination of baculovirus was between $10^2$ and $10^5$ pfu/mL for 50 μL of supernatant.

1 Claim, 6 Drawing Sheets

Figure 1:
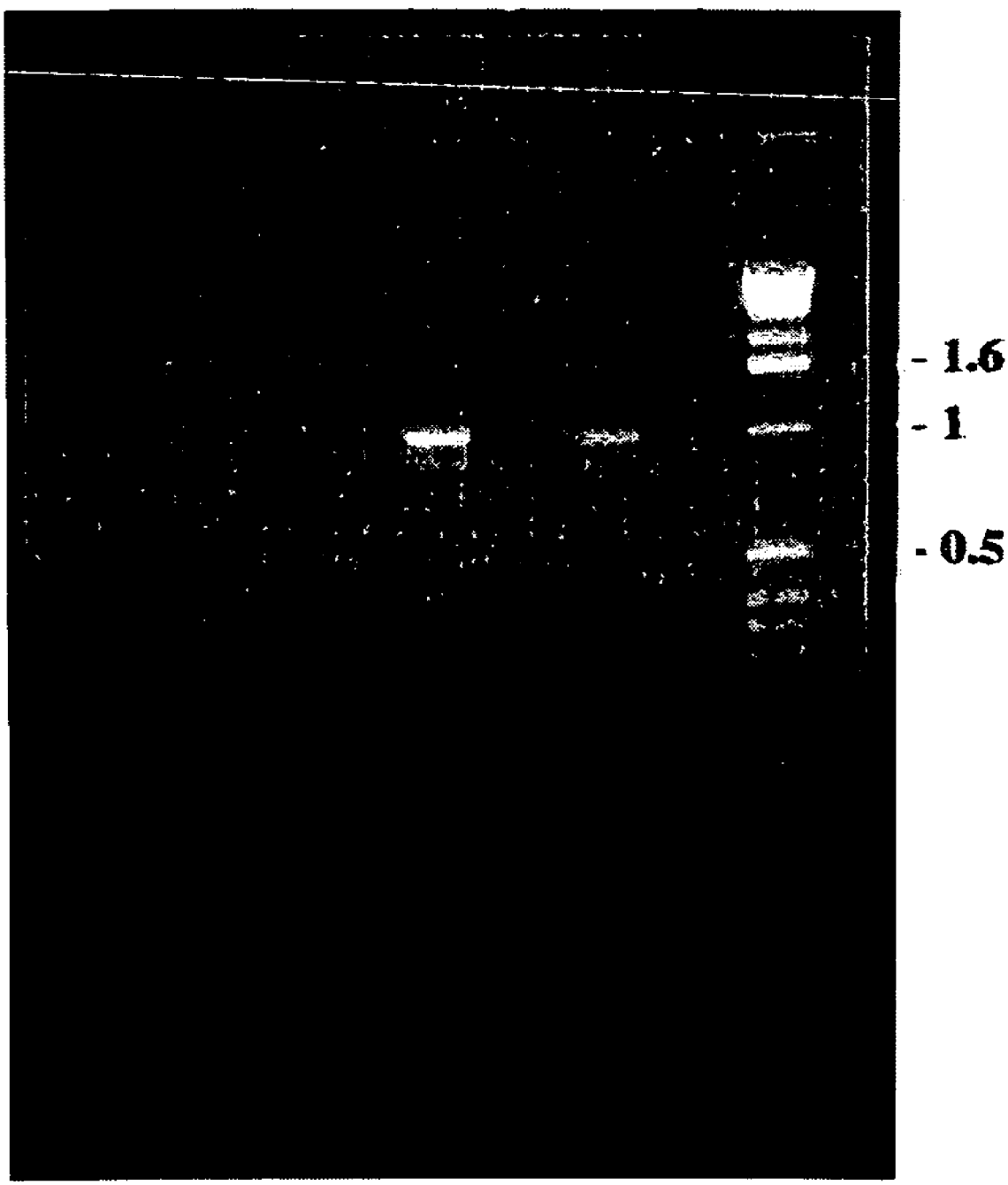

SEQUENCE LISTING

<160> NUMBER OF SEQ ID NOS: 6

<210> SEQ ID NO 1
<211> LENGTH: 23
<212> TYPE: DNA
<213> ORGANISM: baculovirus

<400> SEQUENCE: 1
ggggatccgc aagacatttt gac                23

<210> SEQ ID NO 2
<211> LENGTH: 22
<212> TYPE: DNA
<213> ORGANISM: baculovirus

<400> SEQUENCE: 2
ggcatatggc aactaaacgc aa                 22

<210> SEQ ID NO 3
<211> LENGTH: 20
<212> TYPE: DNA
<213> ORGANISM: baculovirus

<400> SEQUENCE: 3
ccaccggaaa gatcagaaac                    20

<210> SEQ ID NO 4
<211> LENGTH: 20
<212> TYPE: DNA
<213> ORGANISM: baculovirus

<400> SEQUENCE: 4
gtttctgatc tttccggtgg                    20

<210> SEQ ID NO 5
<211> LENGTH: 20
<212> TYPE: DNA
<213> ORGANISM: baculovirus

<400> SEQUENCE: 5
cgactgtcta atttgaacag                    20

<210> SEQ ID NO 6
<211> LENGTH: 20
<212> TYPE: DNA
<213> ORGANISM: baculovirus

<400> SEQUENCE: 6
ctgttcaaat tagacagtcg                    20

UTILIZATION OF NUCLEOTIDE PROBES IN ELISA PROCEDURE FOR THE QUANTITATIVE DETERMINATION OF BACULOVIRUS TITER

FIELD OF THE INVENTION

*Bombyx mori* nucleopolyhedrovirus (BmNPV) and *Autographa californica* nucleopolyhedrovirus (AcNPV) belong to the Baculoviridae, a large family of viruses with double-stranded (ds) DNA genomes that are mainly pathogenic for lepidopteran insects. Both BmNPV and AcNPV are widely employed as vectors for the expression of eukaryotic proteins and pest control. To maximize the yield of protein from a baculovirus system, optimal infection of the host cell culture must be achieved; in order to obtain such optimal infection, the titer of the virus inoculation must be known.

The DNA-binding protein (DBP) has been found to be an early gene product and appears to be crucial for viral DNA replication which leads to viral production. The present invention is the development of a simple, rapid, and universally applicable titration method that involves the direct detection of the viral DBP gene derived from AcNPV (AcNPV DBP) as a target for quantitative titer determination of baculovirus and the use of biotin specific probes directed to viral DBP gene. The procedure for amplifying the AcNPV DBP gene by using the PCR technique in the presence of digoxigenin-11-dUTP from the negative control (non-infected) and infected samples is described. The synthesis of the specific biotin label nucleotide probes directed to the AcNPV DBP gene is performed. These specific probes are then used in the Enzyme Linked Immunosorbent Assay (ELISA) using the immobilized streptavidin on polystyrene microtitration plates for the quantitative determination of baculovirus titer.

BACKGROUND OF THE INVENTION

Baculovirus, including *Bombyx mori* nucleopolyhedrovirus (BmNPV) and *Autographa californica* nucleopolyhedrovirus (AcNPV), belong to a diverse family of arthropod viruses that are characterized by large (80 to 180 kb) circular double-stranded DNA (ds DNA) genomes and rodshaped enveloped virions. BmNPV and AcNPV are widely employed as vectors for the expression of eukaryotic proteins and pest control (Maeda 1989). To maximize the yield of protein from a baculovirus expression system, optimal infection of the host cell culture must be achieved. In order to obtain such optimal infection, the titer of the virus inoculation must be known (King and Possee 1992; Luckow 1993; O'reilly, Miller, and Luckow 1994). Currently, determining the titer of virus stocks is a major time-consuming step in baculovirus gene expression. The most frequently used methods for the titration of baculovirus stocks are end-point dilution and plaque formation (King and Possee 1992; Luckow 1993; O'reilly, Miller, and Luckow 1994). Both the end-point dilution and plaque formation methods require the seeding of cells onto plates, precise 10-fold dilutions of virus stocks, and measurement of viral infection in 4-7 days post virus infection. These are lengthy procedures that are also difficult to perform for scientists who are not familiar with baculovirus expression vector systems. Later on, many other reporter genes, e.g. β-galactosidase (Sussman 1995; Yahata et al. 2000) or green fluorescent protein (GFP) genes (Chao, Chen, and Li 1996; Cha, Gotoh, and Bentley 1997; Wilson et al. 1997), were used in order to more easily detect viral infections; although these reporters improved the sensitivity of detection, they did not significantly reduce the time and effort needed to obtain a titer. To reduce the time for titer determination, several methods were further developed in recent years. Kitts and Green (1999) developed an immunological assay for the determination of baculovirus titers; this technology can determine the titer of a given virus stock within 48 hours. However, in this procedure, cell seeding, virus dilution and infection is still tedious. In 2002, Knon, Dojima, and Enoch developed an antibody-based assay that detects early viral gene products, DNA-binding protein (DBP), in order to determine the titer of baculoviruses; by the detection of early viral gene products, this method could determine the titer of the virus within 10 hours. However, this antibody-based titration assay using expression of DBP is a laborious process which is not reliable due to the fluctuation of the yield of the DBP expression from one cell to another which may lead to inaccurate titer determination; moreover, the rabbit polyclonal antibodies against the DBP used are not adequate enough to recognize DBP specifically. Recently, Lo and Chao (2004) developed a quantitative real-time polymerase chain reaction (Q-PCR) for titer determination of baculovirus. This method is based on the quantitative amplification of the 150-bp fragments of viral DNA using the Q-PCR technique. However, this procedure is laborious, costly and not suited for any laboratory interested in research related to baculoviruses. Indeed, this Q-PCR technology requires many labor-intensive steps for the extraction of highly pure viral DNA using the commercial column and for the construction of recombinant viruses; in addition, performing the Q-PCR titration assays require the use of the expensive LightCycler instrument that not all laboratories can afford to have. Thus, the current situation of the field shows that there is a need to design an easy, simple, and cost-effective procedure for quantitative titer determination of baculoviruses. To address this issue, the present invention offers a new procedure using an approach different from previous ones. The new procedure involves the DBP gene derived from AcNPV (AcNPV DBP) as a target for the development of a simple, rapid, and universally applicable titration method. This procedure entails the amplification of the AcNPV DBP gene by using the PCR technique in the presence of digoxigenin-11-dUTP and the synthesis of the specific biotin label nucleotide probes directed to the AcNPV DBP gene. These specific probes are then used in the Enzyme Linked Immunosorbent Assay (ELISA) for the quantitative determination of baculovirus titer.

PURPOSE OF THE INVENTION

The purpose of the invention is to develop an easy, simple, and cost-effective procedure for quantitative titer determination of baculovirus in order to maximize the yield of protein from a baculovirus system. In order to determine optimal infection conditions, titer determination must be determined accurately. Accurate titer determination depends on the capability of infection detected as soon as the baculovirus is present in the insect cells. The procedure based on the presence of viral DBP gene allows the direct detection of the presence of baculovirus which leads to accurate titer determination. Titer determination depending upon a second phenomenon based on the DBP expression is a process that is not reliable due to the fluctuation of the yield of the DBP expression from one cell to another which may lead to inaccurate determination of the titer. In line with this requirement, the present invention offers a new method that involves the direct detection of the viral DBP gene derived from AcNPV (AcNPV DBP) as a target for quantitative titer determination of baculovirus and the use of biotin specific probes directed to viral DBP gene.

The method of the present invention entails the following procedure: 1/Amplifying the AcNPV DBP gene by using the PCR technique in the presence of digoxigenin-11-dUTP from the negative control (non-infected) and infected samples; 2/Performing the synthesis of the specific biotin label nucleotide probes directed to the AcNPV DBP gene; 3/Performing the ELISA procedure using the immobilized streptavidin on polystyrene microtitration plates for the quantitative determination of baculovirus. This is a simple, easy to operate and cost-effective procedure that allows the quantitative determination of baculovirus titer. Moreover, because of the homology of sequences concerning the DBP gene between BmNPV and AcNPV (96% homology), specific biotin label nucleotide probes obtained from this procedure could be used as a universal tool for titer determination of both viruses.

Materials and Methods

Cell Line, Baculovirus and Culture Medium

*Spodoptera frugiperda* (Sf-9) cells (Pharmingen, San Diego, Calif, U.S.A.) were maintained as monolayer culture in a 96-well plate (Costa$^R$) at 28° C. in TNM-FH medium (Sigma, St. Louis, Mo., U.S.A.) supplemented with 0.35 g/L NaHCO$_3$, 10% (V/V) fetal bovine serum (Sigma, St. Louis, Mo., U.S.A.), and 1% antibiotic-antimycotic (Gibco BRL$^R$, Rockville, Md., U.S.A.). *Autographa californica* nucleopolyhedrovirus -(AcNPV) (Pharmingen, San Diego, Calif., U.S.A.) was used.

Titer Determination of Baculovirus

For titer determination of baculovirus, the following steps are taken.

Infected Cells

A number of the Sf-9 cells (100 µL/well and 4×10$^4$ cells/well) were infected by directly adding AcNPV (50 µL/well) to the Sf-9 cell cultures with the following endpoint serial dilutions of the virus stock (1×10$^8$ pfu/mL): 10$^{-2}$, 10$^{-3}$, 10$^{-4}$, 10$^{-5}$, 10$^{-6}$, 10$^{-7}$, and 10$^{-8}$.

Negative Control

For the negative control (Sf-9 cell cultures not infected), the supplemented TNM-FH medium (50 µL/well) was added.

Infection Assays

The plate was incubated at 27° C. for 5 days and then, whether the cells were infected or not, the 50 µL of the medium was removed and subjected to the isolation of AcNPV particles and AcNPV DNA by using the procedure of the Baculovirus Expression Vector System (Instruction Manual, Pharmingen). The isolated AcNPV DNA was then dissolved in 10 µL of 10 mM Tris-HCl (pH 8.1), 1 mM Na$_2$EDTA. The AcNPV DNA was used as template for the amplification of AcNPV DBP gene.

Amplification in the Absence of Digoxigenin-11-dUTP

The amplification of the AcNPV DBP gene was assessed by the polymerase chain reaction (PCR) technique (Saiki et al. 1985; Kawasaki and Wang 1989). Two synthesized oligonucleotides, forward primer (a) and reverse primer (b) (Invitrogen, Carlsbad, Calif., U.S.A.), which generated appropriate sites (NdeI and BamHI sites), were used. These synthesized oligonucleotides have the following sequences:

5' GGGGATCCGCAAGACATTTTGAC 3' (a) (forward primer)
and
5' GGCATATGGCAACTAAACGCAA 3' (b) (reverse primer)

The oligonucleotide (a) (forward primer) was based on the sequence between base pairs 21135 to 21149 of the AcNPV DNA described by Ayres et al. (1994) (GenBank Accession No. NC_001623). The oligonucleotide (b) (reverse primer) was selected by taking the complementary sequence between base pairs 22117 and 22133 of the AcNPV DNA described by Ayres et al. (1994). Amplification was conducted by using a DNA Thermal Cycler (Amplitron$^R$ II Thermolyne). The reaction was conducted in a total volume of 50 µL with 2.5 units of Taq DNA polymerase (Invitrogen, Carlsbad, Calif.) in the presence of the PCR reaction buffer from the Invitrogen kit containing 2×10$^3$ nM each of oligonucleotides, 200 µM each of nucleotides dATP, dCTP, dGTP, and dTTP, 12.5×10$^2$ nM of MgCl$_2$ and 1 µL of the solution of AcNPV DNA obtained previously. Amplification conditions were as follow: Denaturing at 94° C. for 1 min, annealing at 55° C. for 2 min, and elongation at 72° C. for 1 min, each, unless otherwise noted, for 20 cycles. The PCR products were analyzed by electrophoresis on a 20 g/L agarose gel to screen for the presence of the appropriate-size band using the fluorescent dye ethidium bromide.

Amplification in the Presence of Digoxigenin-11-dUTP

Amplifying the AcNPV DBP gene by the PCR technique (Saiki et al. 1985; Kawasaki and Wang 1989) was also performed in the presence of 10 µM of digoxigenin-11-dUTP (Roche), 190 µM of dTTP, 200 µM each of nucleotides dATP, dCTP, dGTP. The same conditions for PCR were used as described previously. The PCR products were analyzed by electrophoresis on a 20 g/L agarose gel to screen for the presence of the appropriate-size band using the fluorescent dye ethidium bromide. The labeling of nucleic acids with digoxigenin was visualized by transfer of the DNA fragments to 40 cm$^2$ of the nitrocellulose membrane according to the transfer technique described by Southern (1975). The nitrocellulose membrane was then blocked in 12 mL/cm$^2$ of blocking solution (2% bovine serum albumin, BSA, in phosphate-buffered saline, PBS). After incubation for 1 h at 37° C., the nitrocellulose membrane was washed with PBS and then incubated for 1 h at 37° C. in 12 mL/cm$^2$ of blocking solution containing 0.1% Tween$^R$20 and 3 µL of anti-digoxigenin antibody from sheep, conjugated with alkaline phosphatase (Boehringer Mannheim, GmbH, Germany). Then, the nitrocellulose membrane was washed with PBS and alkaline phosphatase activity was measured in the presence of chemiluminescent substrate (CDP-Star™; Boehringer Mannheim, GmbH, Germany). After incubation for 5 min at room temperature, autoradiography was developed using the BIOMAX™MR emulsion film (Eastman Kodak Co., Rochester, N.Y. 14650, USA).

Construction of the Biotin Labeled Nucleotide Probes

Amplification

The AcNPV DBP gene was used as target for titer determination of baculovirus. The synthesis of three specific biotin label nucleotide probes 7, 8, and 9 directed to the AcNPV DBP gene was performed. The AcNPV DNA was first used as template for the amplification of the three DNA fragments 1, 2, and 3 of the AcNPV DBP gene using the synthesized oligonucleotides (a) and (c) for the fragment 1, (d) and (e) for the fragment 2, (f) and (b) for the fragment 3. The sequences of the oligonucleotides (c), (d), (e), and (f) are as follow:

```
5' CCACCGGAAAGATCAGAAAC 3'  (c) (reverse primer)

5' GTTTCTGATCTTTCCGGTGG 3'  (d) (forward primer)

5' CGACTGTCTAATTTGAACAG 3'  (e) (reverse primer)

5' CTGTTCAAATTAGACAGTCG 3'  (f) (forward primer)
```

The oligonucleotides (c) and (e) (reverse primers) were based on the sequences between base pairs 21411 to 21430 and 21811 to 21830, respectively, of the AcNPV DNA described by Ayres et al. (1994) (GenBank Accession No. NC_001623), in this case, however, taking the complementary sequence to allow PCR. The oligonucleotides (d) and (f) (forward primers) were based on the sequences between base pairs 21411 to 21430 and 21811 to 21830, respectively, of the AcNPV DNA described by Ayres et al. (1994) (GenBank Accession No. NC_001623). The PCR reaction was conducted in a total volume of 50 µL with 2.5 units of Taq DNA polymerase (Invitrogen, Carlsbad, Calif., U.S.A.) in the presence of the PCR reaction buffer from Invitrogen kit containing $2\times10^3$ nM each of oligonucleotides, 200 µM each of nucleotides dATP, dCTP, dGTP, and dTTP, $12.5\times10^2$ nM of $MgCl_2$ and 1 µL of the solution of AcNPV DNA obtained previously. Amplification conditions were as follow: Denaturing at 94° C. for 1 min, annealing at 65° C. for 2 min, and elongation at 72° C. for 1 min, each for 35 cycles. The PCR products obtained were the DNA fragments 1, 2, and 3 which were analyzed by electrophoresis on a 20 g/L agarose gel to screen for the presence of the appropriate-size band using the fluorescent dye ethidium bromide. The DNA fragments 1, 2, and 3 were then isolated by phenol-chloroform extraction, dried and resuspended in distilled water according to the method described by Sambrook et al. (1989).

Cloning

The obtained purified DNA fragments 1, 2, and 3 were then subjected to the ligation reactions in the pCR$^R$ II plasmid vector of the TA Cloning kit (Invitrogen, Carlsbad, Calif.). The reagents of this kit and the reaction conditions used were according to the manufacturer's recommendations. The ligation product was then introduced in TOP10F'E. Coli strain by using the reagents and the transformation procedure of the TA Cloning kit (Invitrogen, Carlsbad, Calif., U.S.A.). The screening for inserts was performed by using blue-white color selection. The sequencing of obtained inserts was performed by using the ABI DNA sequencer. The resulting vectors (pCR$^R$ II/DNA$_{1,2,3}$) were termed 4, 5, and 6 for the pCR$^R$ II/DNA$_1$, pCR$^R$ II/DNA$_2$, and pCR$^R$ II/DNA$_3$ respectively.

Synthesis of the Biotin Label probes

From the previously obtained vectors 4, 5, and 6, the EcoRI fragments containing the DNA fragments 1, 2, and 3 respectively, were isolated and used as templates for the synthesis of three specific biotin label nucleotide probes 7, 8, and 9 respectively. The reaction was conducted in the presence of the reagents for the preparation of biotinylated probes (BioPrime$^R$ DNA Labeling System, Invitrogen, Carlsbad, Calif.). The primers (a) and (c), (d) and (e), (f) and (b) were used for the synthesis of the specific probes 7, 8, and 9 respectively. The reaction conditions used were according to the manufacturer's recommendations. The labeling of nucleotide probes with biotin was visualized using the same conditions as that used for visualization of digoxigenin-labeled nucleic acids. Here, 15 µL of anti-biotin-monoclonal antibody conjugated with alkaline phosphatase (Boehringer Mannheim, GmbH, Germany) in 12 mL/cm$^2$ of blocking solution containing 0.1% (V/V) Tween$^R$ 20 were used.

Use of Biotin Labeled Nucleotide Probes in ELISA Procedure

Immobilized streptavidin on polystyrene microtitration plates (SigmaScreen™, Streptavidin coated plate) (Sigma, St. Louis, Mo., U.S.A.) were used for the assays. All washes were performed four times with PBS containing 0.05% (V/V) Tween$^R$ 20 (PBS-T). The substrate solution for alkaline phosphatase (p-nitrophenyl phosphate, pNPP, 1 g/L in 0.2M Tris-HCl buffer, pH 7) was from Sigma, St. Louis, Mo., U.S.A. After incubation for 30 min at 37° C., the reaction was stopped by the addition of 3M NaOH (50 µL per well). The optical density at 405 nm ($O.D._{\lambda=405\ nm}$) was measured in a microplate colorimeter (Molecular Devices, Thermomax Microplate Reader).

For the assays, the AcNPV DNA isolated from negative controls and infected assays with AcNPV were first subjected to PCR in the presence or absence of digoxigenin-11-dUTP as described above. An aliquot of 5 µL of each PCR product was removed and added to a mixture composed of 15 µL of hybridization solution (4× standard saline citrate, SSC, 40% formamide, 40× Denhardt), 6 µL of salmon sperm DNA (1 mg/mL), 5 µL of biotin-labeled nucleotide probes 7, 8 or 9 and 29 µL of distilled water. After denaturation at 97° C. for 10 min, hybridization was performed for 1 h at 42° C. After hybridization, 55 µL of the reaction medium was removed and added to the immobilized streptavidin plates. After incubation for 1 h at 37° C., the plates were washed, and 100 µL of a 1 in 1,000 dilution of alkaline phosphatase antibody anti-digoxigenin, Fab fragments (Roche) in PBS-T containing 2% BSA (PBS-T-BSA) was added. After being incubated again for 1 h at 37° C., the plates were washed, and the substrate solution for alkaline phosphatase was added.

Results and Discussion

Amplification of AcNPV DBP Gene

The results of the study show that the PCR product DBP-DNA of 1,012 bp of the AvNPV DBP gene was successfully amplified in the presence or absence of digoxigenin-11-dUTP by using two synthesized oligonucleotides (a) and (b) (FIG. 1). The analysis of the PCR product DBP-DNA completely matched with the sequences of AcNPV DBP gene described by Ayres et al. (1994) (GenBank Accession No. NC_001623).

Synthesis of Biotin Label Probes

Figure 2:
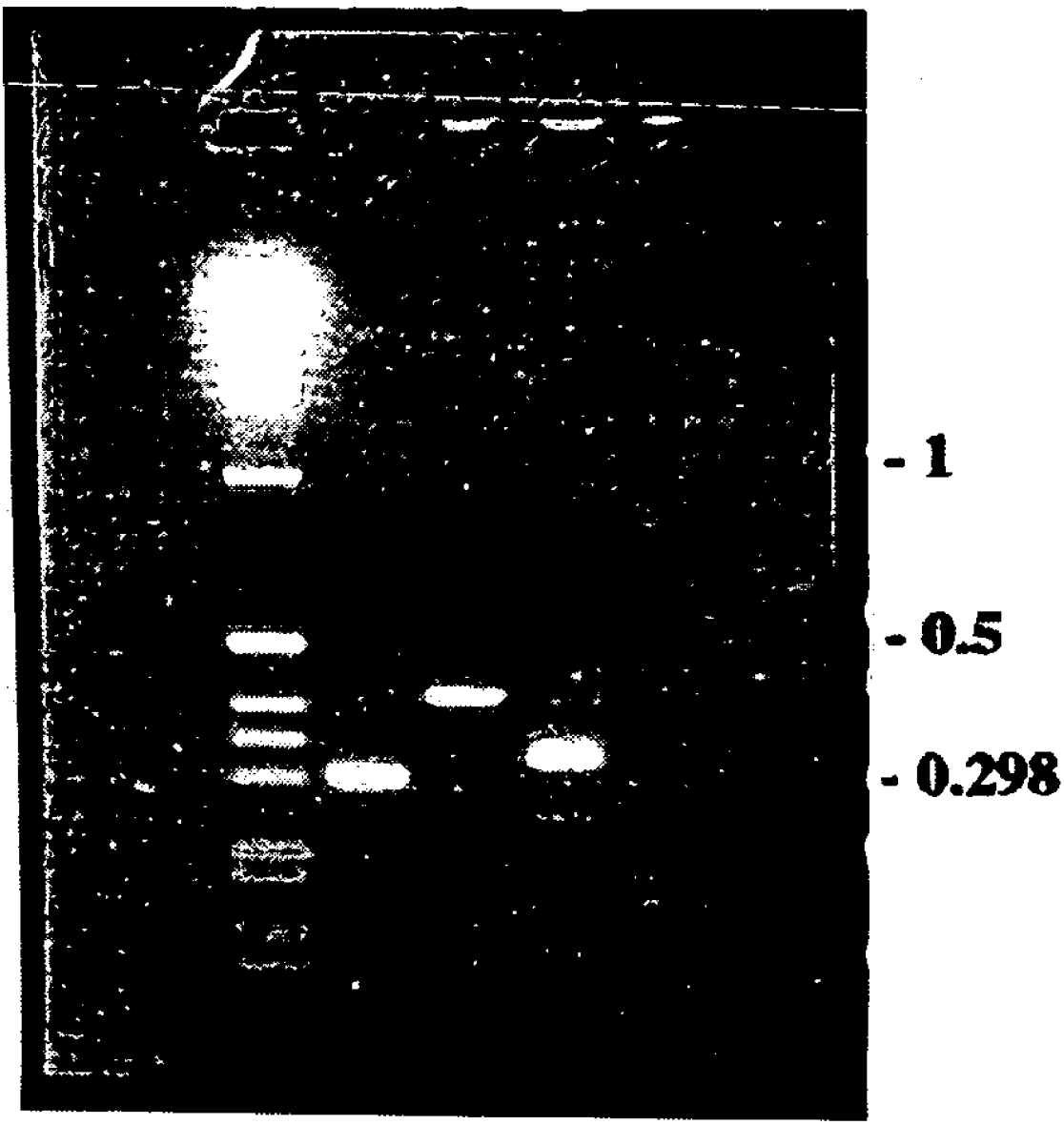

As shown in FIG. 2, the PCR products of the DNA fragments 1, 2, and 3 of 304 bp, 420 bp, and 328 bp respectively were successfully amplified by using the synthesized oligonucleotides (a) and (c), (d) and (e), (f) and (b) for the DNA fragments 1, 2, and 3 respectively. These DNA fragments 1, 2, and 3 were subcloned into the pCR$^R$ II plasmid vector of 3.9 kb. The analysis of the sequence of inserts showed that the DNA sequence of these DNA fragments 1, 2, and 3 completely matched with the sequences of AcNPV DBP gene described by Ayres et al. (1994) (GenBank Accession No. NC_001623). The isolated EcoRI fragments containing the DNA fragments 1, 2, and 3 were used as templates for the synthesis of three specific biotin label nucleotide probes 7, 8, and 9 respectively. All of these three probes 7, 8, and 9 are directed to the AvNPV DBP gene. The efficiency of these probes 7, 8, and 9 (0.56 ng each) was found in the ELISA procedure for the detection of AcNPV DBP gene from the PCR products obtained for 35 cycles of amplification of AcNPV DBP in the presence or absence of digoxigenin-11-dUTP (FIG. 1). In the absence of digoxigenin-11-dUTP, the results showed that the $O.D._{\lambda=405\ nm}$ obtained with the PCR products for amplification of AcNPV DBP gene were 0.156, 0.149; 0.147, 0.138; 0.127, 0.134 for the probes 7, 8, and 9 respectively (Table 1). These $O.D._{\lambda=405\ nm}$ values correspond to the backgrounds. The mean background values corresponding were then 0.152, 0.142, and 0.130 for the probes 7, 8, and 9 respectively. In this study, an $O.D._{\lambda=405\ nm}$ value higher than twice the mean background value was considered as a suitable cutoff, i.e. 0.304, 0.284, and 0.260 for the probes 7, 8, and 9 respectively. Therefore, all samples yielding an $O.D._{\lambda=405\ nm}$ value greater than 0.304, 0.284, and 0.260 for the probes 7, 8, and 9 respectively were considered positive for infection, whereas those with an $O.D._{\lambda=405\ nm}$ value less than these cutoff values were scored as negative; also, because the $O.D._{\lambda=405\ nm}$ values obtained from the substrate solution for alkaline phosphatase (0.174, 0.156, 0.138) are similar to those of the backgrounds (Table 1), the $O.D._{\lambda=405\ nm}$ values obtained for the substrate solution for alkaline phosphatase can be used for the determination of the cutoff value. In this case, the mean background value is 0.156 and the cutoff value is 0.312. In the presence of digoxigenin-11-dUTP, there was a perfect concordance of the results obtained between the ELISA procedure and the electrophoresis analysis of the PCR products on the 20 g/L agarose gel regarding the negative control and positive sample (FIG. 1 and Table 1). All $O.D._{\lambda=405\ nm}$ values obtained for the negative control were significantly less than the cutoff values (0.244, 0.218, and 0.188 for the probes 7, 8, and 9 respectively (Table 1). Concerning the positive sample, all $O.D._{\lambda=405\ nm}$ values obtained were much greater than the cutoff values (1.267, 1.734, and 0.902 for the probes 7, 8, and 9 respectively). Therefore, all three specific probes 7, 8, and 9 directed to the AcNPV DBP gene are very effective for the detection of the presence of AcNPV DBP gene in the infected Sf-9 cells. The probe 8 appears as the best one for this purpose because the highest value of $O.D._{\lambda=405\ nm} =1.734$ was obtained (Table 1).

Quantitative Determination of Baculovirus Titer

PCR Conditions

Figure 3A:
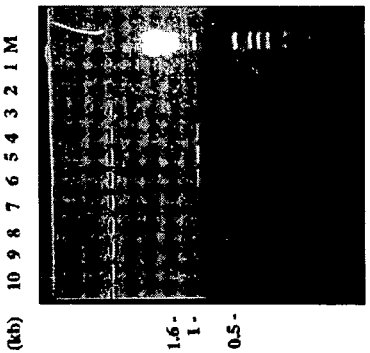
Figure 3B:
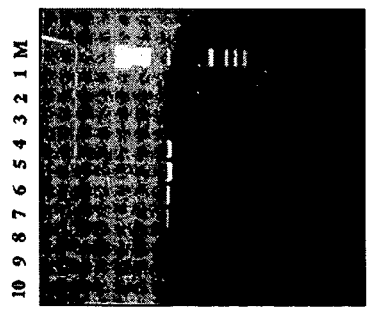
Figure 3C:
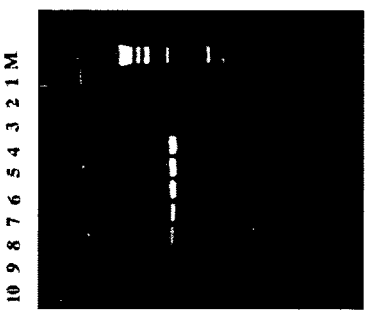
Figure 3D:
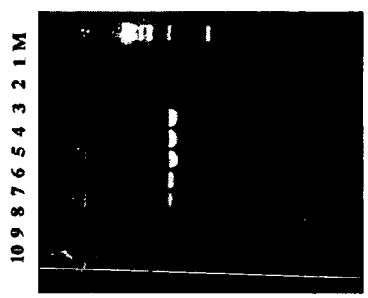

In order to explore the possibility for quantitative measurement of the PCR products (AcNPV DBP gene), the different cycles ranging from 15 to 35 cycles of the PCR reaction using the isolated AcNPV DNA as template were performed. Then, the isolated AcNPV DNA from the negative controls and infected samples using different dilutions of the virus stock ranging from $10^{-2}$ to $10^{-8}$ were subjected to the PCR reaction. The results provided in FIG. 3b show that a quantitative measurement of the AcNPV DBP gene can be performed with the PCR reaction for 20 cycles. Indeed, all PCR products were not present for 15 cycles of the PCR reaction; there was no PCR products with the dilutions of $10^{-5}$, $10^{-6}$, $10^{-7}$, and $10^{-8}$ of the virus stock (see lanes 7, 8, 9, and 10 3a). However, the PCR products obtained with the dilutions of $10^{-5}$ and $10^{-6}$ of the virus stock were present for 20 cycles, and very much present for 25 cycles and 35 cycles of amplification (see lanes 7, 8 in FIGS. 3b, 3c, and 3d). Finally, there was no PCR products (even after 35 cycles of amplification) with the dilutions of $10^{-7}$ and $10^{-8}$ of the virus stock, i.e., there was no AcNPV infection with these dilutions of $10^{-7}$ and $10^{-8}$ of the virus stock (see lanes 9, 10 in FIG. 3d). Consequently, the 20 cycles of the PCR reaction were selected to ensure quantitative measurements during the linear phase.

Titer Determination

Figure 4:
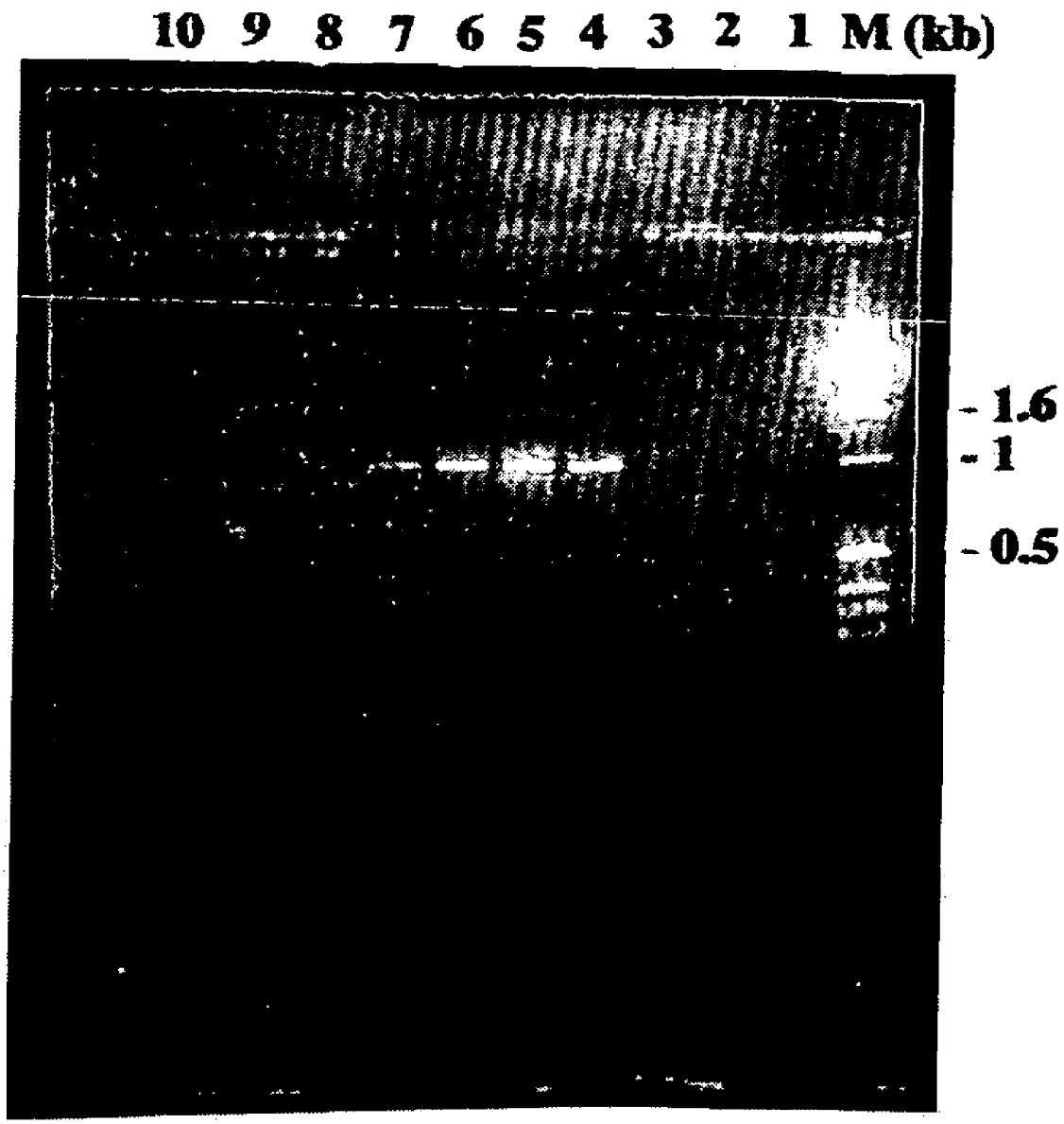

For titer determination of baculovirus, the isolated AcNPV DNA from the controls and infected samples using different dilution of the virus stock ranging from $10^{-2}$ to $10^{-8}$ as mentioned above were subjected to the PCR reaction in the presence of digoxigenin-11-dUTP and for 20 cycles. The electrophoresis analysis of the PCR products on the 20 g/L agarose gel was shown in FIG. 4. The same results as shown in FIG. 3b (PCR reaction for 20 cycles of amplification in the absence of digoxigenin-11-dUTP) concerning the PCR products obtained with the dilutions of $10^{-2}$, $10^{-3}$, $10^{-4}$, $10^{-5}$, and $10^{-6}$ of the virus stock were obtained (FIG. 4).

The results of titer determination of baculovirus by ELISA technique using the specific probe 8 alone (0.56 or 1.4 ng) as well as the results obtained from the cooperative effect in combination use of the specific probes 7, 8, and 9 (0.56 ng each) are presented in Table 2; here, the cutoff value of 0.312 based on the $O.D._{\lambda=405\ nm}$ values of the substrate solution for alkaline phosphatase (Table 1) was used for the consideration of AcNPV positive or negative infection. The obtained ELISA results show an increase of the capability of AcNPV infection with the decrease of dilution of the virus stock (Table 2). A maximum of AcNPV infection was observed with the dilution of $10^{-3}$ of the virus stock; when the dilution of the virus stock is less than $10^{-3}$, there was a decrease of AcNPV infection as observed with the dilution of $10^{-2}$ of the virus stock (Table 2). There was a perfect concordance between the results obtained from the quantitative ELISA procedure and the results from the electrophoresis analysis of the PCR products on the 20 g/L agarose gel for the probe 8 alone (1.4 ng) and for the combination use of the probes 7, 8, and 9 (0.56 ng each) (Table 2 and FIG. 4). However, there was a discordance between the results obtained from the quantitative ELISA procedure and the results obtained from the electrophoresis analysis of the PCR products for the probe 8 alone when it was used at a dose of 0.56 ng (Table 2 and FIG. 4). Indeed, with this dose of 0.56 ng of the probe 8 alone, the ELISA results obtained with the dilutions of $10^{-5}$, $10^{-6}$ of the virus stock were scored as AcNPV negative infection (Table 2). The dose of 0.56 ng of the probe 8 alone was not quantitatively enough for titer determination of baculovirus. The ELISA results obtained by using the specific probe 8 alone (1.4 ng) as well as the results obtained from the cooperative effect in combination use of the specific probes 7, 8, and 9 (0.56 ng each) (Table 2) were exploited: The plot of the $O.D._{\lambda=405\ nm}$ against the log. of the titer (pfu/mL) generated a straight line in each case, specific probe 8 alone (1.4 ng) in FIG. 5, and the combination use of the probes 7, 8, and 9 (0.56 ng each) in FIG. 6. The results for both cases thus show that the linear range for titer determination of baculovirus was between $10^2$ and $10^5$ pfu/mL. The linear regression equations where y is the $O.D._{\lambda=405\ nm}$ and x the log. of the titer (pfu/mL): y=0.4812x−0.5909, $r^2$=0.9722 is for the use of the probe 8 alone (1.4 ng) (FIG. 5), and y=0.2852x−0.2227, $r^2$=0.9645 is for the combination use of the probes 7, 8, and 9 (0.56 ng each) (FIG. 6) respectively. The validity of these two calibration curves were tested by using different virus stocks with known original titers; the test results show that the titers found are similar (data not shown). These results thus show that the plots are reliable and can be used for the quantitative determination of baculovirus titer.

CONCLUSION

The innovation described herein is the procedure which involves the use of biotin specific probes 7, 8, and 9 directed to the AcNPV DBP gene in the ELISA procedure in order to quantitatively determine baculovirus titer. The reliability of this method was demonstrated in the region of $10^2$ to $10^5$ pfu/mL for 50 μL of supernatant. Unlike previous approaches developed to determine baculovirus titer, the new method of the present invention is simple, easy to operate and cost-effective. Moreover, because of the homology of sequences concerning DBP gene between BmNPV and AcNPV (96% homology), the synthesized biotin specific probes 7, 8, and 9 could be used as a universal tool for titer determination of both baculoviruses.

LEGEND OF FIGURES

FIG. 1: PCR amplification of the AcNPV DBP gene in the presence or absence of digoxigemn-11-dUTP.
M: Marker (kb)
Lane 1: Negative control (AcNPV non-infected sample)-absence of digoxigenin-11-dUTP
Lane 2: AcNPV infected sample (dilution of $10^{-4}$ of the virus stock of $1\times10^8$ pfu/mL)-absence of digoxigenin-11-dUTP
Lane 3: Negative control (AcNPV non-infected sample)-presence of digoxigenin-11-dUTP
Lane 4: AcNPV infected sample (dilution of $10^{-4}$ of the virus stock of $1\times10^8$ pfu/mL)-presence of digoxigenin-11-dUTP FIG. 2: PCR amplification of the DNA fragments located in the coding region of the AcNPV DBP gene.
Lane 1: Fragment 1 (304bp)
Lane 2: Fragment 2 (420bp)
Lane 3: Fragment 3 (328bp)

FIG. 3: Quantitative PCR conditions for amplifying AvNPV DBP gene in the absence of digoxigenin-11-dUTP and ranging from 15 to 35 cycles (3a: 15 cycles; 33c: 25 cycles; 3d: 35 cycles).
M: Marker (kb)
Lanes 1 to 3: Negative controls (AcNPV non-infected samples)
Lanes 4 to 10: AcNPV infected samples (dilutions of $10^{-2}$, $10^{-3}$, $10^{-4}$, $10^{-5}$, $10^{-6}$, $10^{-7}$, and $10^{-8}$ of the virus stock of $1\times10^8$ pfu/mL for the lanes 4 to 10 respectively).

FIG. 4: Quantitative PCR amplification for 20 cycles of the AcNPV DBP gene in the presence of digoxigenin-11-dUTP.
M: Marker(kb)
Lanes 1 to 3: Negative controls (AcNPV non-infected samples)
Lanes 4 to 10: AcNPV infected samples (dilutions of $10^{-2}$, $10^{-3}$, $10^{-4}$, $10^{-5}$, $10^{-6}$, $10^{-7}$, and $10^{-8}$ of the virus stock of $1\times10^8$ pfu/mL for the lanes 4 to 10 respectively).

Figure 5:
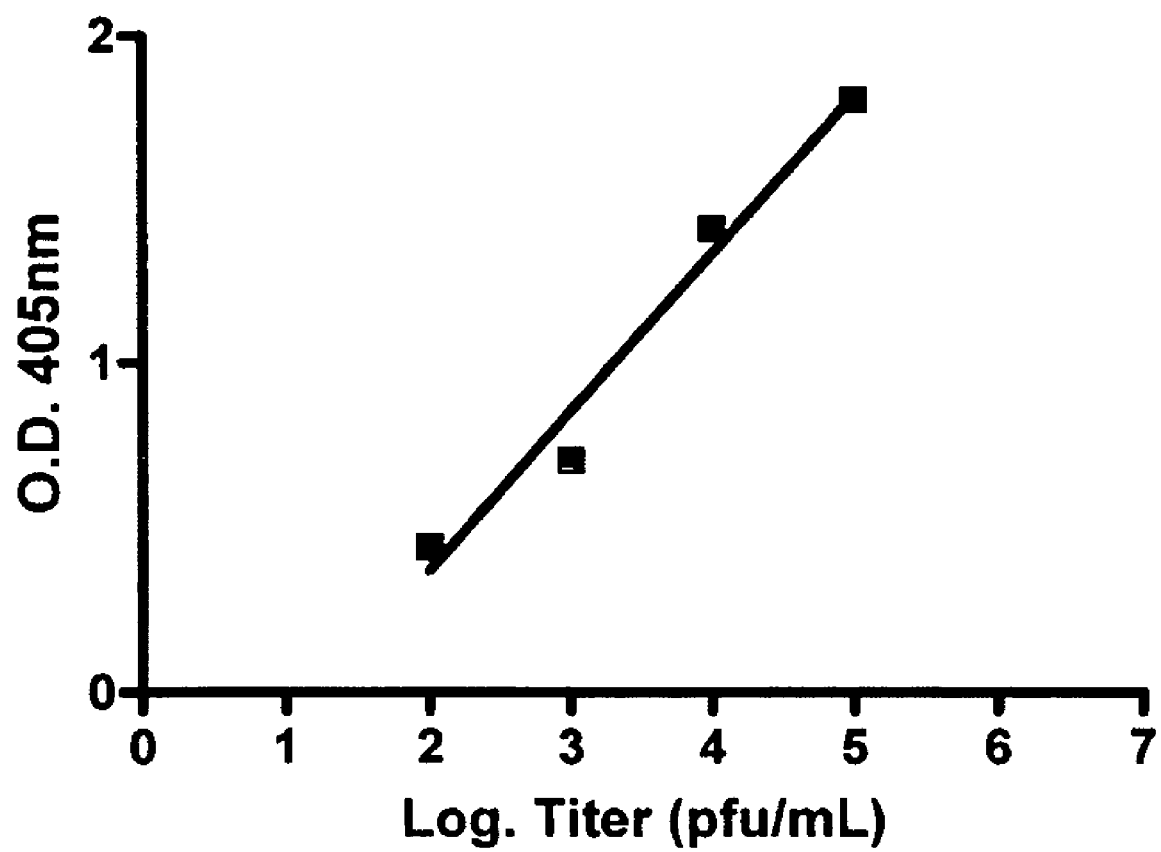

FIG. 5: Standard curve for the determination of baculovirus titer by using the biotin label probe 8 alone (1.4 ng). Each point represents the average value from duplicate samples with a relative mean deviation lower than 1%. The line is drawn by linear regression where y is the $O.D._{\lambda=405nm}$ and x the log of the titer (pfu/mL) (y=0.4812x−0.5909, $r^2$=0.9722).

Figure 6:
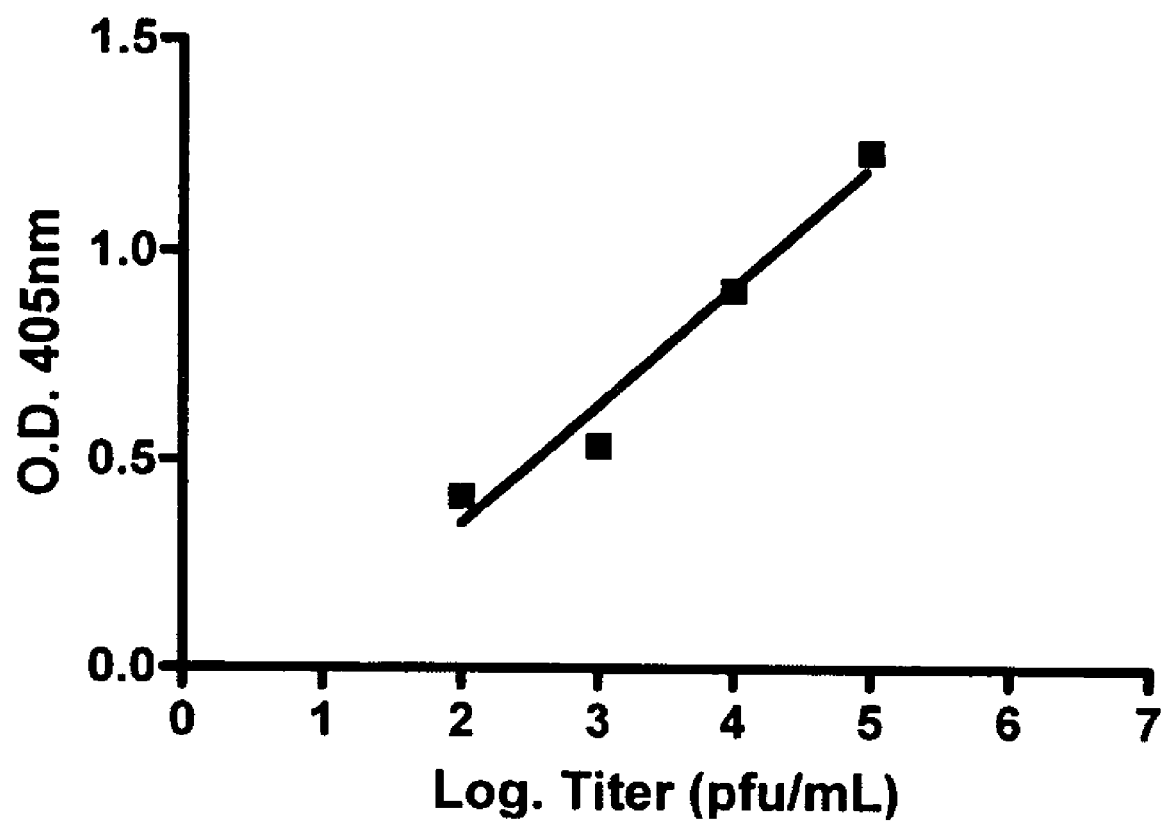

FIG. 6: Standard curve for the determination of baculovirus titer by combination use of the biotin label probes 7, 8, and 9 (0.56 ng each). Each point represents the average value from duplicate samples with a relative mean deviation lower than 1%. The line is drawn by linear regression where y is the $O.D._{\lambda=405nm}$ and x the log of the titer (pfu/mL) (y=0.2852x−0.2227, $r^2$=0.9645).

TABLE 1

Efficiency of the biotin label probes 7, 8, and 9 for the detection of AcNPV DBP gene determined by ELISA[a],[b],[c] ($O.D._{\lambda=405nm}$).

| Biotin label probes No. | Absence of digoxigenin-11-dUTP Lanes No. | | Presence of digoxigenin-11-dUTP Lanes No. | |
|---|---|---|---|---|
| | 1 | 2 | 3 | 4 |
| 7 | 0.156 | 0.149 | 0.244 | 1.267 |
| 8 | 0.147 | 0.138 | 0.218 | 1.734 |
| 9 | 0.127 | 0.134 | 0.188 | 0.902 |

[a] The $O.D._{\lambda=405nm}$ values of the substrate solution for alkaline phosphatase are 0.174, 0.156, and 0.138.
[b] Lanes 1 and 3: Negative control (AcNPV non-infected sample)
[c] Lanes 2 and 4: AcNPV infected sample (dilution of $10^{-4}$ of the virus stock of $1 \times 10^8$ pfu/mL)

TABLE 2

Quantitative detection of AcNPV DBP gene determined by ELISA[a],[b],[c] ($O.D._{\lambda=405nm}$).

| Biotin label probes No. | Negative controls Lanes No. | | | Infected samples Lanes No. | | | | | | |
|---|---|---|---|---|---|---|---|---|---|---|
| | 1 | 2 | 3 | 4 | 5 | 6 | 7 | 8 | 9 | 10 |
| 8 (0.56 ng) | 0.190 | 0.194 | 0.198 | 0.566 | 0.726 | 0.512 | 0.234 | 0.189 | 0.129 | 0.192 |
| 8 (1.4 ng) | 0.180 | 0.151 | 0.178 | 1.519 | 1.809 | 1.415 | 0.706 | 0.442 | 0.150 | 0.150 |
| 7 + 8 + 9 (0.56 ng each) | 0.133 | 0.152 | 0.151 | 1.055 | 1.240 | 0.911 | 0.537 | 0.414 | 0.146 | 0.142 |

[a] The $O.D._{\lambda=405nm}$ values are the mean of duplicate.
[b] Lanes 1 to 3: Negative controls (AcNPV non-infected samples)
[c] Lanes 4 to 10: AcNPV infected samples (dilutions of $10^{-2}$, $10^{-3}$, $10^{-4}$, $10^{-5}$, $10^{-6}$, $10^{-7}$, $10^{-8}$ of the virus stock of $1 \times 10^8$ pfu/mL for the lanes 4 to 10 respectively and this corresponds to a baculovirus titer of $10^6$, $10^5$, $10^4$, $10^3$, $10^2$, 10, and 1 for the lanes 4 to 10 respectively).

What is claimed is:

1. The procedure using the specific biotin label nucleotide probes directed to the baculovirus DNA-binding protein (DBP) gene, *Bombyx mori* nucleopolyhedrovirus DBP gene (BmNPV DBP gene) and *Autographa californica* nucleopolyhedrovirus DBP gene (AcNPV DBP gene), for the quantitative determination of baculovirus titer, comprising:

The procedure for amplifying the AcNPV DBP gene from the negative control (non-infected) and AcNPV infected samples, based on the polymerase chain reaction (PCR) in the presence of digoxigenin-11-dUTP using the synthesized oligonucleotides (SEQ ID NO. 1) and (SEQ ID NO. 2) for PCR:

Isolating of AcNPV DNA from the negative control and AcNPV infected samples;

Using the oligonucleotides 5'GGGGATCCGCAAGA-CATTTTGAC 3'(SEQ ID NO. 1) and 5'GGCATATGGCAACTAAACGCAA 3'(SEQ ID NO. 2) to perform PCR reaction, under PCR conditions: Denaturing at 94° C. for 1 minute; annealing at 55° C. for 2 minutes; elongating at 72° C. for 1 minute each cycle, for 20 cycles;

The procedure for the synthesis of three specific biotin label nucleotide probe 7, synthesized using SEQ ID NOs 1 and 1, probe 8, synthesized using SEQ ID NOs 4 and 5 and probe 9, synthesized using SEQ ID NOs 6 and 2, directed respectively to the three different fragments of 304 bp (fragment 1), 420 bp (fragment 2), and 328 bp (fragment 3) located in the coding region of the AcNPV DBP gene using the synthesized oligonucleotides (SEQ ID NO. 1) and (SEQ ID NO. 3) for fragment 1, (SEQ ID NO. 4) and (SEQ ID NO. 5) for fragment 2, (SEQ ID NO. 6) and (SEQ ID NO. 2) for fragment 3:

Isolating of AcNPV DNA from the AcNPV infected sample;

Using the oligonucleotides 5' CCACCGGAAAGATCAGAAAC 3' (SEQ ID NO. 3) 5' GTTTCTGATCTTTCCGGTGG 3' (SEQ ID NO. 4) 5' CGACTGTCTAATTTGAACAG 3' (SEQ ID NO. 5) and 5' CTGTTCAAATTAGACAGTCG 3' (SEQ ID NO. 6) to perform PCR reaction, under PCR conditions: Denaturing at 94° C. for 1 minute; annealing at 65° C. for 2 minutes; elongating at 72° C. for 1 minute each cycle, for 35 cycles;

Ligating the PCR product into the $pCR^R$ II plasmid vector and introducing the ligation product in TOP10F' *E. Coli* strain;

Screening for inserts based on the presence of white colonies that results in the selection of the vectors 4 ($pCR^R$ II/$DNA_1$), 5 ($pCR^R$ II/$DNA_2$), and 6 ($pCR^R$ II/$DNA_3$);

Isolating the EcoRI fragments containing the DNA fragments 1, 2, and 3 from the obtained vectors 4, 5, and 6 and using these DNA fragments 1, 2, and 3 as templates for the synthesis of three specific biotin label nucleotide probes 7, 8, and 9 by using the synthesized nucleotides (SEQ ID NO. 1) and (SEQ ID NO. 3) for the probe 7, (SEQ ID NO. 4) and (SEQ ID NO. 5) for the probe 8, (SEQ ID NO. 6) and (SEQ ID NO. 2) for the probe 9;

The ELISA procedure for the determination of the titer of baculovirus using the obtained specific label nucleotide probes 7, 8, and 9, the obtained amplified Ac NPV DBP gene conjugated to digoxigenin-11-dUTP, and the immobilized streptavidin on polystyrene microtitration plates:

Taking an aliquot of 5 μL of the amplified AcNPV DBP gene conjugated to digoxigenin-11-dUTP obtained from the negative control and AcNPV infected samples as described above;

Adding to a mixture of 15 μL of hybridization solution (4×standard saline citrate, SSC, 40% formamide, 40× Denhard), 6 μL of salmon sperm DNA (1 mg/mL), 5 μL of biotin labeled nucleotide probes 7, 8, or 9) and completing to a final volume of 60 μL with water;

Denaturating at 97° C. for 10 minutes;

Hybridizing for 1 hour at 42° C.;

Removing 55 μL of the reaction medium and adding to the immobilized streptavidin plates;

Incubating for 1 hour at 37° C.;

Washing the plates with phosphate-buffered saline (PBS) containing 0.05% (V/V) $Tween^R$ 20 (PBS-T);

Adding 100 μL of a 1 in 1,000 dilution of alkaline phosphate antibody anti-digoxigenin (Fab fragments) in PBS-T containing 2% bovine serum albumin, BSA (PBS-T-BSA);

Incubating for 1 hour at 37° C.;

Washing the plates with PBS-T;

Adding 200 μL of the substrate solution for alkaline phosphatase;

Incubating for 30 minutes at 37° C.;

Stopping the reaction by adding 50 μL of 3M NaOH;

Measuring the optical density (O.D.) at 405 nm.

* * * * *